United States Patent
Tikanoja et al.

(10) Patent No.: US 9,891,149 B2
(45) Date of Patent: Feb. 13, 2018

(54) METHOD AND APPARATUS FOR AUTOMATED ANALYSIS

(75) Inventors: Sari Tikanoja, Vantaa (FI); Annu Suoniemi-Kähärä, Vantaa (FI); Johan Finell, Vantaa (FI); Lili Arabshahi, Fremont, CA (US)

(73) Assignee: Thermo Fisher Scientific Oy, Vantaa (FI)

( * ) Notice: Subject to any disclaimer, the term of this patent is extended or adjusted under 35 U.S.C. 154(b) by 263 days.

(21) Appl. No.: 13/568,803

(22) Filed: Aug. 7, 2012

(65) Prior Publication Data

US 2013/0040307 A1 Feb. 14, 2013

Related U.S. Application Data

(60) Provisional application No. 61/515,992, filed on Aug. 8, 2011, provisional application No. 61/623,082, filed on Apr. 12, 2012.

(30) Foreign Application Priority Data

Aug. 8, 2011 (FI) .................................. 20115785
Apr. 12, 2012 (FI) .................................. 20125401

(51) Int. Cl.
*G01N 1/00* (2006.01)
*G01N 1/40* (2006.01)
(Continued)

(52) U.S. Cl.
CPC .......... *G01N 1/405* (2013.01); *G01N 35/025* (2013.01); *G01N 2035/1039* (2013.01); *Y10T 436/25125* (2015.01)

(58) Field of Classification Search
USPC .............. 422/62, 63, 64, 67, 68.1, 69, 73; 436/175, 177, 178, 43; 530/412, 413,
(Continued)

(56) References Cited

U.S. PATENT DOCUMENTS 4,030,888 A * 6/1977 Yamamoto ............ G01N 35/00
                                                    356/39
4,764,601 A    8/1988 Reuning et al.
(Continued)

FOREIGN PATENT DOCUMENTS

WO   WO 2004/096443 A1   11/2004
WO   WO 2007/064635 A1   6/2007
(Continued)

OTHER PUBLICATIONS

Kamaneva et al. ("Effects of Turbulent Stresses upon Mechanical Hemolysis: Experimental and Computational Analysis" ASAIO Journal 2004 pp. 418-423 DOI: 10.1097/01.MAT.0000136512. 36370.B5).*
(Continued)

*Primary Examiner* — Chris L Chin
(74) *Attorney, Agent, or Firm* — Seppo Laine Oy

(57) ABSTRACT

A method for pretreatment of a sample of whole blood in a discrete fluid analyzing instrument comprises automated means for handling and analyzing the sample and means for performing a pretreatment step on the sample or a sub-sample of the sample. The means for pretreatment are used for immobilizing at least one substance or analyte from the sample or sub-sample wherein the substance or analyte is reversibly immobilized. Usually, the apparatus further comprises means for eluting the substance or analyte from the capture means prior to analysis.

38 Claims, 4 Drawing Sheets

(51) Int. Cl.
*G01N 35/02* (2006.01)
*G01N 35/10* (2006.01)

(58) Field of Classification Search
USPC .................. 530/414, 415, 416, 418, 422
See application file for complete search history.

(56) References Cited

U.S. PATENT DOCUMENTS

| | | | |
|---|---|---|---|
| 5,030,554 A * | 7/1991 | Quintana et al. ............... 435/2 |
| 5,116,578 A | 5/1992 | Baxter | |
| 5,260,192 A | 11/1993 | Russell et al. | |
| 5,439,813 A | 8/1995 | Anton et al. | |
| 5,731,211 A * | 3/1998 | Ohlin ........................ 436/179 |
| 5,812,419 A | 9/1998 | Chupp et al. | |
| 5,858,974 A | 1/1999 | Little et al. | |
| 5,891,734 A * | 4/1999 | Gill ........................ B01F 5/0453 422/63 |
| 5,939,326 A * | 8/1999 | Chupp ..................... B01F 5/0453 422/63 |
| 5,985,153 A | 11/1999 | Dolan et al. | |
| 6,344,172 B1 | 2/2002 | Afeyan et al. | |
| 7,897,337 B2 | 3/2011 | Macioszek et al. | |
| 2004/0058387 A1 | 3/2004 | Sakurai et al. | |
| 2004/0124128 A1 | 7/2004 | Iwata | |
| 2005/0069913 A1 | 3/2005 | Mian et al. | |
| 2006/0204997 A1 | 9/2006 | Macioszek et al. | |
| 2006/0275906 A1* | 12/2006 | Devlin, Sr. ................. 436/43 |
| 2009/0090855 A1 | 4/2009 | Kobold et al. | |
| 2009/0162942 A1 | 6/2009 | Platano et al. | |
| 2009/0253210 A1 | 10/2009 | Kobold et al. | |
| 2010/0112682 A1 | 5/2010 | Boyette et al. | |
| 2010/0286114 A1 | 11/2010 | Thomas et al. | |
| 2011/0070664 A1 | 3/2011 | Woolley et al. | |
| 2011/0275162 A1 | 11/2011 | Xie et al. | |
| 2012/0134895 A1 | 5/2012 | Kanda et al. | |
| 2012/0185177 A1 | 7/2012 | Hannon et al. | |
| 2012/0206713 A1 | 8/2012 | Nogami et al. | |
| 2013/0040307 A1 | 2/2013 | Tikanoja et al. | |

FOREIGN PATENT DOCUMENTS

| | | | | |
|---|---|---|---|---|
| WO | WO 2008/016414 A2 | 2/2008 | | |
| WO | WO 2009-046227 A1 | 4/2009 | | |
| WO | WO 2009/121034 A2 | 10/2009 | | |
| WO | WO 2009121034 A2 * | 10/2009 | ............ | G01N 35/10 |
| WO | WO 2010135382 A1 | 11/2010 | | |
| WO | WO 2011/019032 A1 | 2/2011 | | |
| WO | WO 2011/063416 A2 | 5/2011 | | |

OTHER PUBLICATIONS

Laboratory Procedure Manual, Tosoh A1c 2.2 Plus Glycohemoglobin Analyzer, Steffes, 2007-2008.*
Steffes, Laboratory Procedure Manual, Tosoh G7 Glycohemoglobin Analyzer, 2011-2012.*
Tosoh G7 HPLC Analyzer brochure, no date available.*
Karl-Siegfried Boos, "Cell-Disintegrated Blood (CDB): A Unique Substitute for Dried Blood Spots (DBS)," Laboratory of BioSeperation, Institute of Clinical Chemistry, Medical Center of the University of Munich, Munich, Germany, Apr. 20, 2010 (pp. 1-48).
Karl-Siegfried Boos, et al., "Trends in der SPE-LC-MS Analyse von Pharmaka in Biogischen Flussigkeiten," Laboratorium fur BioSeparation, Institut fur Klinische Chemie, Klinikum der Universitat Munichen, Nov. 12-13, 2007.
Finnish Search Report, dated Dec. 9, 2014, for Finnish Application No. 20125401.
Reynolds et al., "Early Biomarkers of Stroke," Clinical Chemistry, vol. 49, No. 10, 2003, pp. 1733-1739.
United States Office Action, dated Feb. 9, 2015, for U.S. Appl. No. 13/568,965.
Mark A. Reynolds et al: "Early Biomarkers of Stroke", Clinical Chemistry 49:10, 2003, pp. 1733-1739.
Merriam Webster 1998.

* cited by examiner

FIG. 4

METHOD AND APPARATUS FOR AUTOMATED ANALYSIS

CROSS REFERENCE TO RELATED APPLICATIONS

This nonprovisional application claims the benefit under 35 U.S.C. § 119(e) of U.S. Provisional Application Nos. 61/515,992 filed on Aug. 8, 2011 and 61/623,082 filed on Apr. 12, 2012 and under 35 U.S.C. § 119(a) of Patent Application Nos. 20115785 filed in Finland on Aug. 8, 2011 and 20125401 filed in Finland on Apr. 12, 2012. The entire content of all of the above applications is hereby incorporated by reference.

The present invention relates to method and apparatus for automated sample treatment for automated discrete fluid analyzer

BACKGROUND OF THE INVENTION

Several chemical analyses are done by automatic analyzing equipment in hospitals and laboratories. The level of automation varies, but present trend is to streamline the analyzing work as much as possible. As many more complicated analyses must be performed manually by highly trained laboratory personnel, the productivity and throughput of such laboratory testing services has been low. By increasing the automation capabilities of the laboratory, more of the work can be performed inside the automatic systems without involvement of highly skilled personnel. Ideally laboratory assistants simply load samples in racks into the analyzing apparatuses freeing laboratory chemists and biologists to focus on interpreting the results and managing the operation of the laboratory. Such a system provides good throughput combined with high certainty and quality of analytical results.

Automated instruments for various kind of chemical analysis have been widely used for decades. They may combine both routine and sophisticated assay techniques such as spectrophotometry, fluorometry, time resolved fluorometry, chromatographic methods etc. with automated sample dispensing from original sample containers. Automation is often required as test workload increases within healthcare and clinical laboratories, public or commercial research and service institutes, or industrial process control.

Automatic discrete analysis techniques use computer controlled automation to perform steps similar to those of manual methods. For example, a computer controlled robotic arm may be used to position a probe of a pipette to aspirate or deposit a fluid sample, buffer or reagent into or out of any of a plurality of sample receptacles, a plurality of reagent receptacles and a plurality of reaction cuvettes. This is a "discrete" analysis technique because each sample is deposited in a discrete reaction cuvette, which is then subjected to an assaying device such as colorimetric photometer, or the like. Typically several discrete analyses may be done on subsamples divided from a main sample placed on a receptacle. For example, from a serum sample, a panel of serum lipids (triglycerides, cholesterol and HDL-cholesterol) can be measured.

Many sample types, particularly human samples for clinical testing, are not ready for assay as collected and, instead, require a pretreatment step. For example, plasma or serum must be separated from whole blood; whole blood must be hemolyzed to release intracellular components; fecal, sputum or solid tissue samples must be homogenized and suspended in liquids. In many cases of human excretions or other biological and industrial materials, interfering proteins must be precipitated, or analytes extracted from the original sample matrix. So while automatic analyzers have significantly improved throughput rate of analytical testing service, manual sample pretreatment has become a primary bottleneck in daily work flow.

Manual processes not only add to the time and labor required to produce results but also increase the risk of errors. Errors during the analytical process have been addressed primarily by automation as automation standardizes pipetting and dispensing steps, and eliminates variation in timing and differences between individual technicians. Sample pretreatment, however, remains prone to problems and would benefit from automation as well.

To increase sample throughput and provide process standardization, some automated or semi-automated sample pretreatment instruments have been developed. These are mainly meant to be used in connection with highly sophisticated analysis techniques that require sample purification steps before the actual measurement can be performed. For example, TurboFlow™ columns (Thermo Fisher Scientific) are used to separate small molecules from proteins or other large molecules in a sample before introduction to a LC/MS system. For PCR techniques, desired cell types must often be selected from complex sample mixtures for further treatment, and sample DNA or RNA must be purified to substantially eliminate background contamination before the actual cycling process. Semi-automated pretreatment instruments like those based on magnetic particles, e.g. the KingFisher™ instrument (Thermo Fisher Scientific), are useful for such processes.

Publications WO 2004096443, US 2005069913, U.S. Pat. Nos. 5,985,153 and 7,897,337 disclose examples of automated pretreatment methods and apparatuses and fully automated analyzing processes including pretreatment of all input samples. These are mainly used for DNA and RNA analysis wherein pretreatment is needed for all samples before analysis can be performed. Contamination risk is also extremely high. Usually disposable sample containers are needed, as well as disposable pipette tips or dispensers for transporting samples, sample aliquots, analytes and reagents.

However, many laboratories must function without such sophisticated automated or semi-automated equipment. Typically, the main daily workload of many clinical laboratories is performed using low-cost automated analyzers based on simple analytical techniques such as photometry or spectrophotometry. Such analyzers usually employ conventional assay methods that provide result levels traditionally considered sufficient for measurement of clinically significant ranges. Many compromises concerning acquired information and accuracy are made in order to achieve acceptable cost and speed while providing ease of use and maintenance.

Sample pretreatment is often considered as a separate process from the actual assay and, therefore, not well suited to instruments streamlined to perform one type of analytical process or measurement quickly and efficiently. Pretreatments are designed according to sample matrix and nature of analyte, and are usually not bound to particular assay principles. This may explain the lack of pretreatment automation, as sample oriented additional steps preceding the chemical assay reaction would lower throughput and cause difficulty in timing of assay sequences.

Despite difficulties in combining pretreatment processes with automatic discrete analysis, some pretreatment systems have been combined to automatic analysis apparatuses. Some of these systems are described below for reference.

On-Board Pretreatment of Whole Blood in Discrete Photometric Analyzers in the Measurement of Glycated Hemoglobin A1c (HbA1c).

In on-board methods to measure HbA1c, a sample of whole blood is hemolyzed within a discrete photometric analyzer to release the hemoglobin molecules from within blood cells. Hemolyzation is carried out by mixing whole blood with hemolyzing reagent in a reaction vessel or a cuvette and incubating the mixture for a defined time. After hemolyzation, an aliquot of the mixture is sampled to measure HbA1c content with a turbidimetric inhibition immunoassay and another aliquot is sampled to measure total hemoglobin content. In such method, the analytes and matrix components are not separated prior to the analyzing. This kind of analysis can be performed by Konelab™ clinical chemistry analyzers (Thermo Fisher Scientific), for example.

Cadmium Column Reduction of Nitrate

In a cadmium column, nitrate ($NO_3-$) is reduced to nitrite ($NO_2-$) using $Cd_{2+}$ granules as catalyst. The reduction is accomplished by aspirating sample to the column where the reduction takes place and then eluting the reduced sample to a vessel. From the vessel an aliquot is sampled to measure nitrite. This kind of analysis can be performed by an Aquakem™ analyzer (Thermo Fisher Scientific). In this system analytes undergo a chemical reaction during the pretreatment; there is no means for separating reacted from unreacted or other non-target analytes. The nitrate reduction to nitrite can also be performed in a reaction vessel.

US 2009/0162942 discloses an automated discrete fluid sample analyzer that includes a sample preparation module. The sample preparation module includes a well configured to receive a sample deposited by a pipette and a sample preparation device in fluid communication with the well. The fluid sample is transferred from the well to the sample preparation device which prepares the sample by using catalyst, ultraviolet light or heat. The target analyte is not separated from the sample.

Samples of whole blood may have to be pretreated also in order to release a target analyte from components within the sample that bind or sequester the analyte. This can be done by preparation of a secondary specimen i.e. blood plasma or serum by centrifugation or filtration. A hemolysis reagent like saponin or detergent may be added followed by centrifugation or filtration. Likewise a denaturing agent may be used, e.g. acid (HCl, TCA) or an organic solvent (methanol, acetonitrile) or a combination of methanol and ZnSO, followed by centrifugation. These protocols involve manual steps which are difficult to automate or integrate into an on-line analysis procedure. In order to increase the degree of automation, an automated on-line hemolysis processor referred to as a Bloodlyser® device has been described (Morello, R. et al. *Ther Drug Monit* 29:143, 2007). As used, a sedimented blood sample is mixed by an autosampler procedure And the homogenized sample is pumped through a stainless steel capillary heated to 75° C. and the resulting heat causes no precipitation of blood/plasma proteins yet results in complete disintegration of blood cells. This leads to generation of new matrix referred to as "cell-disintegrated blood" by the developers of the process.

SUMMARY OF THE INVENTION

The present invention provides a novel approach to arrange integrated pretreatment for automated discrete analyzing apparatus.

According to one preferred embodiment of the invention a whole blood sample is hemolyzed and at least one matrix substance or analyte is retained from the sample volume by capture means wherefrom it is reversibly removable.

According to embodiments of the invention, the hemolysis is performed by use of (i) capillary device at room temperature capable of applying a shearing force to physically rupture cellular components, (ii) sonication, (iii) detergents or other chemicals to disrupt cell membranes, (iv) mild heat, followed by processing using an affinity column or other preparatory column capable of capturing the analyte or matrix component(s) or (v) using a heated capillary device.

According to one preferred embodiment, the matrix substance or analyte that is retained, is eluted or regenerated from the capture means for measurement.

According to one preferred embodiment, analyte is retained.

According to one embodiment of the invention, the analyte is retained by a method that is chemically inactive in relation to the analyte that is measured from the pretreated volume.

According to another aspect and embodiment of the present invention, the invention provides a method wherein the analyte to be measured is retained by immobilization.

According to one specific feature of the invention, the invention utilizes a surface that immobilizes the substance that is to be measured.

At least one embodiment of the invention enables to enrich analytes. Enrichment is needed when the concentration of analytes in the sample is too low for the measurement. This can be done by retaining the analytes in, for example a column, or other suitable apparatus, and eluting them in a volume that is smaller than the initial volume.

At least one embodiment of the invention enables the separation of analytes and matrix components that interfere with the analyte measurement. This is done either by retaining the analytes in a column or other suitable apparatus, and washing matrix components out before analyte elution, or by retaining the matrix components in the column and washing the analytes out before matrix elution.

According to one preferred embodiment of the invention, an integrated pretreatment step is provided comprising selectively either a pretreatment wherein at least one matrix substance is retained from a sample volume without chemically changing the chemical composition of the analyte or the sample is left untreated, whereafter one or more analysis are performed on the sample.

According to one embodiment of the invention, the measurements are performed with a discrete fluid analyzer that performs chemical reactions and photometric measurements in single/separate wells.

According to one embodiment of the invention, the measurement is at least one of the group comprising photometric measurement or electrochemical measurement.

According to one especially preferred embodiment, at least two different measurements are performed on subsamples of one sample; either after a pretreatment is performed, without performing the pretreatment or both.

According to one embodiment of the invention, dispensing and transportation of subsamples of an analyte sample volume is performed with a non-disposable or an on board washable dispenser or dispenser tip.

According to one embodiment of the invention, at least one measurement is performed on pretreated or not pretreated subsample (sample aliquot) without reacting the subsample chemically.

According to one embodiment of the invention, at least one measurement is performed on pretreated or not pretreated subsample (sample aliquot) after adding at least one reagent thereto.

The above mentioned embodiments may be used at least for:
separating analytes from complexing or binding molecules,
separating analytes from cell debris,
separating analytes from substances interfering with analyte detection,
desalting the sample,
exchanging the sample solvent,
separating analytes from matrix substances.

At least one embodiment of the invention is applicable to fractionation of analytes into different fractions. This is done by retaining the analytes in the column or on other substrates, and eluting the analytes in fractions by using eluents with increasing elution strength.

Isolation and/or concentration of analytes from a sample can be achieved by using one of the following methods, or any combination of two or more, including but not limited to:
immobilization/retention by use of
1) antibodies or other specific binding substances,
2) passive adsorption,
3) covalently binding substances, or
by filtering
concentration via immobilization and elution into reduced volume,
immobilization of a non-target substance from the sample to increase assay specificity,
immobilization of a substance from the sample to avoid interference with assay performance,
partial purification of a sample by immobilization and elution of a substance from a complex mixture of substances,
separation of a target analyte from cell debris,
separation of an analyte from complex forming or binding molecules,
separation or purification of derivatives of the analyte.

The modes by which the retention is accomplished include, but is not limited to, reversible covalent bonding, ionic interaction, sieving or filtering (molecular size and shape, diffusion), polarity, hydrophobicity, molecule or group specific interaction and chiral recognition. One aspect of the invention is to provide a novel hemolyzing process and apparatus wherein the whole blood sample is hemolysed by using a capillary device, for example, a plastic or glass capillary tube, at the prevailing temperature of the sample, usually within a range of 5° C. to 40° C. and more commonly at room temperature, capable of applying a sheering force to physically rupture cellular components. According to alternative embodiments of the invention, the required shear force can be accomplished by using a screening plate or successive plates with small holes, a circular or straight slot between elongated walls or a ceramic, fiber or other type of a filter.

One aspect of the invention is to use capillary devices with an internal diameter of about 1 mm, which are generally suitable for applying a shearing force sufficient to rupture cellular components with a blood sample.

The invention, in one aspect, is an automated discrete fluid analyzing device providing sample pretreatment wherein at least one substance of the sample matrix or analyte is retained.

In another aspect the invention is an automated discrete photometric analyzing device providing sample pretreatment wherein at least one substance of the sample matrix or analyte is retained.

According to one embodiment, at least one substance is retained by immobilizing it to a solid support and eluting it from the solid support for analysis and/or measurement.

According to one embodiment the retained substance is removed from the sample and not subjected to analysis.

According to one embodiment of the invention at least one substance is retained from the sample by a filtration method, such as membrane filtration or a gel filtration.

According to one embodiment of the invention, the at least one substance is retained by immobilization on a solid support.

According to one embodiment of the invention, the at least one substance is retained by immobilization by an antibody.

According to one or more embodiments of the invention, the at least one substance is retained by one or more of following methods: reversible covalent bonding, ionic interaction, sieving or filtering (molecular size and shape, diffusion), polarity, hydrophobicity, molecule or group specific interaction and chiral recognition.

Examples of Sample pretreatment process
Sample contains Analyte(s) of interest (A), Interfering (I) and Other substances (O) and water or other Fluid (F).
In this invention, upon user request by software, subsample is taken and automatically pretreated to bring the unaltered analyte of interest (A) to the discrete photometric analysis.

| No | Sample | Component(s) retained in the pretreatment unit | Component(s) removed from the pretreatment unit | Samples for the discrete photometric analysis |
|---|---|---|---|---|
| 1 | A + F + I + O | A (Analyte) | I + F + O | Analyte is concentrated and/or purified in the pretreatment phase. In the measurement phase analyzer can automatically calculate its original concentration in the sample. Analyte remains intact throughout the process. |
| 2 | A + F + I + O | I (Interfering substance) | A + F + O | Sample is pretreated to clean the interfering substances. Interfering substance(s) (I) are retained in the pretreatment unit. Unaltered analyte is transferred eg. into a secondary |

-continued

Examples of Sample pretreatment process
Sample contains Analyte(s) of interest (A), Interfering (I) and Other substances (O) and water or other Fluid (F).
In this invention, upon user request by software, subsample is taken and automatically pretreated to bring the unaltered analyte of interest (A) to the discrete photometric analysis.

| No | Sample | Component(s) retained in the pre-treatment unit | Component(s) removed from the pretreatment unit | Samples for the discrete photometric analysis |
|---|---|---|---|---|
| 3 | A + F + I + O | Sample is not directed to the pre-treatment unit | | sample holder and further directed to analysis. Thereafter the capturing device is regenerated and elution and regeneration liquids are descarded. Analyte of interest (A) can be calculated to the original concentration in the sample after the discrete photometer measurement for the specific analyte. Sample can also be analyzed as such without the pretreatment step |
| 4 | A + F + I + O | | | Two or more pretreatments in any order |

Other objects and features of the invention will become apparent from the following detailed description considered in conjunction with the accompanying drawings. It is to be understood, however, that the drawings are intended solely for purposes of illustration and not as a definition of the limits of the invention, for which reference should be made to the appended claims.

BRIEF DESCRIPTION OF THE DRAWINGS

FIG. 4 shows an explanatory screen display of an apparatus utilizing the invention.

DETAILED DESCRIPTION OF THE PRESENTLY PREFERRED EMBODIMENTS

In the subsequent text the following terms and devices should be understood to be defined as below:
Pretreatment
Separate step from analysis chemistry; provides e.g. a concentrated, fractionated or purified analyte. In general pretreatment may be modifying or non-modifying in relation to the substance to be pretreated.
Discrete Fluid Analyzer
Discrete fluid analyzer performs chemical reactions and photometric measurements in single/separate wells. Usually an analyzer contains multiple wells in which different reactions are ongoing simultaneously. Several different tests may be requested from each sample. Also different types of samples may be analyzed simultaneously.
Column
Column is typically a cylindrical or other formed vessel to which liquid samples and reagents may be introduced and analytes and/or other components eluted. The column may be in-line connected to a pump or syringe in which case the samples and reagents are pumped to and from the column using positive or negative pressure. Or the column may be freely diffusing in which case samples and reagents are drawn to and from the column by gravity or by centrifugal force. The column may be packed or lined with material that has affinity towards the analytes or matrix components. As an alternative, the column may be packed with material that functions as a sieve or filter. Physical treatments may also be connected to the column.

The column may be single use (disposable) or reusable.
Sample
A whole sample as collected is a "sample" or "primary sample". The part of the sample that is pretreated, is a "sub sample".

The substances that are analyzed are analytes. All other components in a sample are matrix.

The analytes may include, for example: ions, molecules, groups of chemically related substances, substance, family of substances such as proteins and chemical species.

Matrix includes all matter that is not measured, for example: cell debris, substances interfering with analyte measurement, analyte complexing/binding substances that interfere with analyte measurement.

Room temperature is considered to be standard laboratory room temperature (RT) of 25° C.
Washable
Washable means herein a device that can be successively used by cleaning it between consecutive operative steps, opposite to a single use device that is discarded after every contact with analyte or other liquid in order to avoid contamination.

Figure 1:
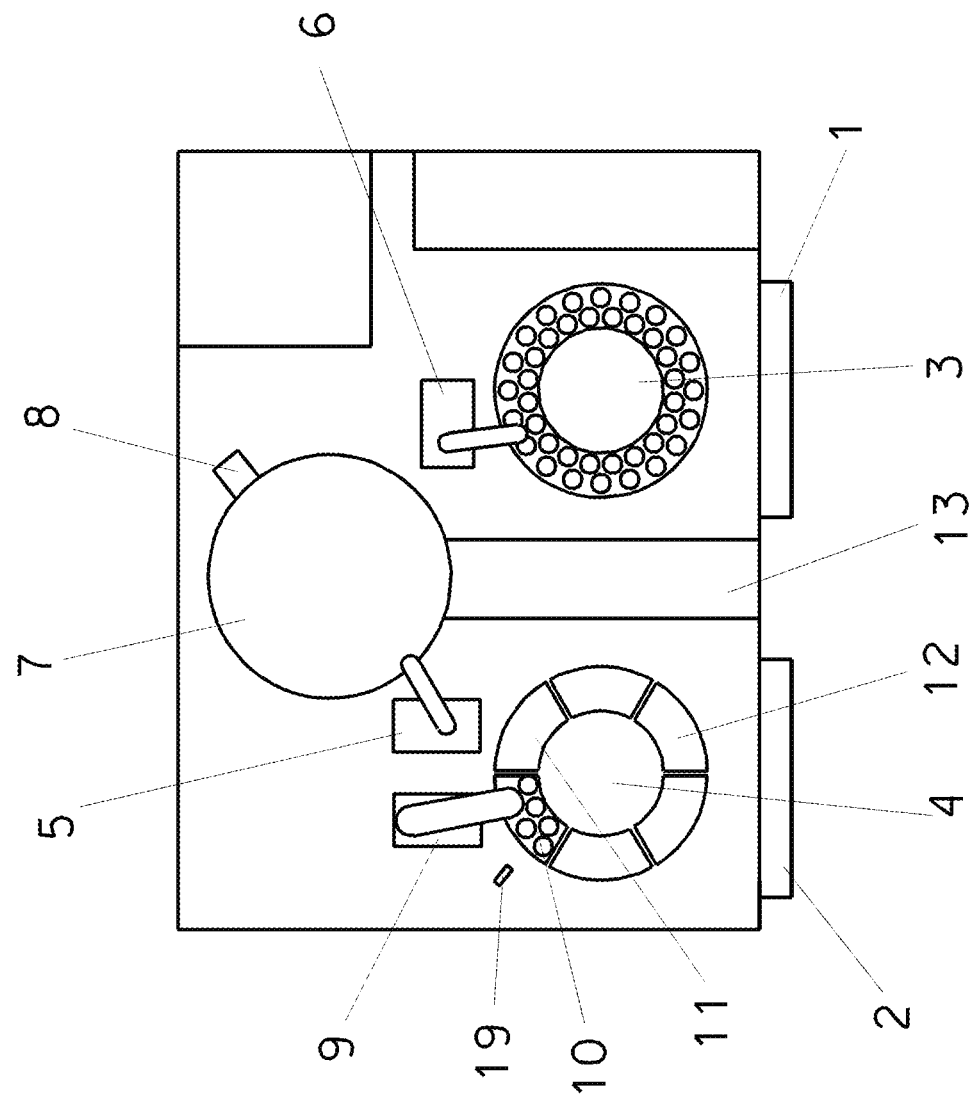
FIG. 1 shows diagrammatically an automated discrete fluid analyzing device to which the invention is implemented.

FIG. 1 shows a typical discrete analyzer. As these apparatuses have been in laboratory use and their operation principles are known to persons skilled in the art or can be easily studied from operating manuals and basic literature, only a cursory description of the apparatus shown in FIG. 1 is provided herein as an example. The invention is not limited to any specific type of an automated discrete analyzing device as long as its operation is controlled by sample handling rules permitting sample handling routines for each sample so that a request to analyze a sample may include an assay of the measurements required and a request for pretreatment if such is desired.

FIG. 1 shows the main elements of an analyzing device. These are arranged on a suitable frame and include diluent water container 1 and waste water container 2. Samples to be analyzed are placed on sample wheel 4 and reagents, enzymes and other media needed for analyses on reagent wheel 3. Samples are handled with sample dispenser 5 and reagents with reagent dispenser 6. Measurements of analytes or components within the samples occur in incubator 7 with a photometer 8.

For the pretreatment of a sample, a pretreatment unit 9 is arranged in relation to sample wheel 4. The sample wheel 4 is divided in sections that form racks 10, 11, 12 arranged as reagent rack 10 for elution and wash liquids, microplate rack 11 for pretreated samples and sample racks 12 for untreated samples. Between the sample and reagent wheels is a cuvette dispenser 13. FIG. 1 represents an exemplary arrangement with other arrangements possible.

In further description of FIG. 1, when pretreatment is not needed for the indicated measurement, cuvettes are fed from the cuvette dispenser 13 to the incubator 7 whereafter sample volumes of the collected sample are aspirated with the sample dispenser 5 into the cuvettes as requested by analyzing assay request of the sample. Accordingly, reagents needed for requested measurements are dispensed by reagent dispenser 6 into the cuvettes and after a measurement specific incubation period, the measurement is performed for each cuvette by photometer.

Figure 2:
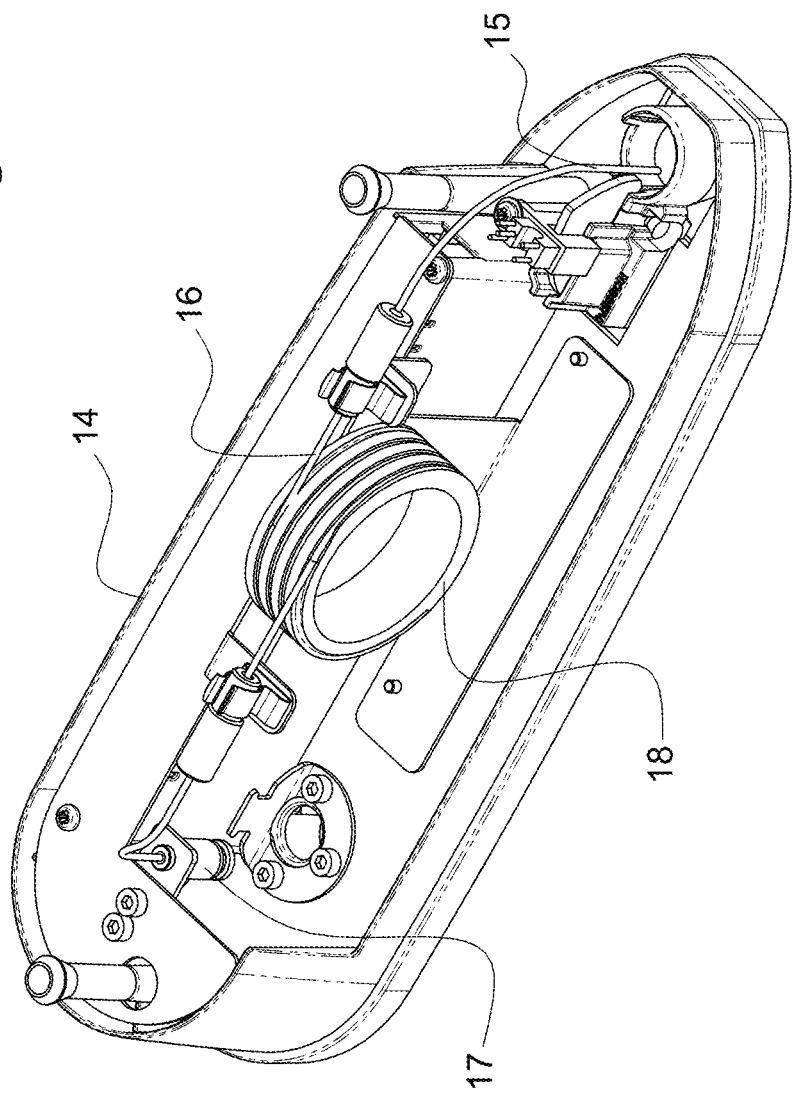
FIG. 2 shows diagrammatically one embodiment of a pretreatment unit for device in FIG. 1.

When the analyzing assay request includes pretreatment, a portion of the sample is aspirated in the pretreatment unit 9. A side view of unit 9 is shown in FIG. 2.

The exemplary pretreatment unit of this embodiment is built on a frame 14 that is rotatably mounted on the analyzing device. The main parts of the pretreatment unit may include a pump for sample aspiration and ejection through line 17. Line 17 connects the pump line to a pretreatment column 16. In order to enable use of a long column 16 and sufficient pretreatment time and to keep the dimensions of the pretreatment unit 9 small, the column shown in this embodiment is on a grooved stationary wheel 18. On the opposite end of the pump 17, the column is connected to a suction or pipetting tube 15 for aspiration and ejection of the sample.

One type of pretreatment column 16 is a column containing internal surfaces that immobilize the analyte from the sample to the surfaces of the column. These surfaces may be walls of the column itself or some filler material, which may be in particle or fibrous form. For pretreatment in such a column the substance must be first retained and then released from the surfaces and placed into cuvettes in for measurements. For this the sample wheel has a reagent rack 10 for elution and wash liquids. Further, FIG. 1 shows a washing station 19 arranged in vicinity of pretreatment unit 9. When a pretreatment is needed, the cycle may start with a washing cycle of the column 16 at the washing station 19, but usually the column 16 is washed at the end of the pretreatment cycle. Washing is performed simply by aspirating water or other washing liquid into the column so that it is substantially filled and then ejecting the washing solution into a waste container 2. The aspiration and ejection is repeated as many time as needed to obtain desired level of purity and the washing liquid may be pumped reciprocatingly in order to increase removing effect.

For pretreatment a desired amount of sample liquid is aspirated into the column 16 through pipetting line 15 and the sample is pumped through the column so that at least the entire sample volume has entered the column. This forms a sub-sample of the original sample, which remains untreated and may be used for other measurements without the effects of pretreatment. In the column, the substance, for example a molecule, is retained and immobilized on the wall or other interior surface of the column. For this, the sample may be kept in the column or pumped reciprocatingly in the column to ensure sufficient reaction time. Heating or cooling of the sub-sample may be used for enhanced effect. After the reaction time needed to immobilize the target analyte has passed, the sample is ejected from the column. The target analyte remains immobilized within the column. In order to make the measurement, the immobilized molecule or substance must be eluted from the surface via washing the column with an elution liquid placed in the reagent rack 10. The elution liquid is ejected together with the substance eluted from the column 16 to a microplate rack 11 to await transfer to the incubator. The measurement of the sample occurs in a routine manner, for example, by a photometer according to operating principles of the analyzing apparatus. Thus, the pretreatment step is merely one additional handling step in the analyzer for the sample and can be arranged within the normal measuring cycle without disturbing the operation of the apparatus or changing the function, construction or operation of the apparatus. The pretreatment unit and washing stations, reagents and elution liquids may be fitted to existing apparatuses without difficulty.

The main problem with handling samples for discrete analyzers is the small volume of the sample. Since the volume of the sample is small, many traditional pretreatment methods like evaporation or treatments based on chemical reactions performed on the substance to be measured are difficult to implement. The present invention provides a solution to this problem by using capture or immobilization methods for either enriching the substance that is measured or its proportion in the sample. This is accomplished by retaining the target analyte or retaining other substances that interfere with the measurement of the target analyte and removing them from the sample. The retaining method itself may vary, but the immobilization method discussed above provides one embodiment suitable for implementation for many various measurements.

Another approach to retaining a substance is adsorption or physical bonding of the substance to a surface or another substance via chemical binding. In practice binding may occur through covalent bonds, electrostatic interactions or van der Waals forces or other surface forces between molecules or substances.

Various pretreatment methods will be discussed below in further detail.

This method of using a pretreatment unit enables transfer of the treated sample into the measurement unit. Transfer is controlled by a user friendly software whereby the instrument user may simply add the primary sample tube in the instrument sample feeding unit and program the desired assay. When a sample pretreatment step is necessary, the software automatically directs the sample into the pretreatment unit, while other analyses from the same sample or other samples continue to be performed without delay or disturbance.

Within the clinical and non-clinical fields, the present invention benefits numerous assays.

For example, many physiologically important compounds including without limitation, Vitamin A, D and E, are fat-soluble and/or bound in circulation to a corresponding binding protein or other protein structures. Serum vitamin D samples must be pretreated in order to disrupt the protein complex and extract the analyte in an organic solvent such as acetonitrile or methanol by a manual procedure. With a pretreatment unit containing a surface for immobilizing the complex formed, the analyte can be eluted by a suitable solvent and then transferred to the assay performing unit. Immobilization may be accomplished by antibody binding or by chemical binding and the surface will be automatically regenerated and washed between samples. A similar separation step may be adapted to many small molecular compounds and thus avoid using instrumentation more complicated than a photometer.

The pretreatment surface may comprise a coated surface inside a glass or metallic column, enabling solid phase extraction. Particles of uniform or different size may be coated and packed in a tube or other column container. Coated fibers or other materials may also be used. The reactive surface may also comprise a microfluistic platform or otherwise comprise liquid pathways molded or printed on various suitable materials. The coating may include antibodies or other specific binders. Also, many chemically reactive surfaces (hydrophilic, hydrophobic, lipophilic, nitrogenous or organic group binding) may be useful. In one embodiment, binding is irreversible or accomplished via bonds from which the substance can be removed and the surface regenerated or comprises equilibrium binding.

Sophisticated and time consuming chromatographic techniques are often used to measure components in mixtures, if there are no simple ways to separate the required analyte from the other constituents. In these cases, the pretreatment unit may comprise a surface coated with an antibody against the analyte which is measured by a standard photometric method.

On the other hand, pretreatment may be used to purify the sample by immobilizing a cross-reacting substance using an antibody against the substance that is coated on the pretreatment surface. The purified sample can then be measured by standard turbidimetry or other methods.

Within some immunoassays antibodies may cross-react with substances related to the desired analyte. Pretreatment to remove such cross-reactants may avoid such problems and antibodies or other binding or marker substances with lower specificity may be used. Such an approach may lead to reductions of the costs of antibody development.

An important application of the invention are assays that today cannot be performed by photometric methods because of their low sensitivity. For instance, the preferred hormone to diagnose thyroid disorders, thyrotrophin-stimulating hormone (TSH), is typically so low in serum concentration that complicated techniques usually performed by separate instruments are used for measurements of TSH. If, however, an immunoaffinity pretreatment method for TSH is used to concentrate TSH approximately 10-fold or more, a useful turbidimetric assay is possible.

For food safety, analysis of various toxic mycotoxins in agricultural products is very important. For concentration and separation from sample matrices, extractions and immunoaffinity steps are necessary prior to assay. These steps may be automated by using specific antibodies or mycotoxin group binders for solid phase extraction in the pretreatment unit.

A similar approach is useful in environmental analysis when measuring cyanotoxins, produced by Cyanobacteria.

In the brewery industry, certain iso-alpha-acids are monitored during the brewing process to estimate bitterness of beer. The reference method used employs extraction with iso-octane. This procedure may be omitted and the assay automated by using pretreatment where the target iso-alpha-acids are bound to a surface and then eluted by a suitable solvent, to be transferred to measurement unit.

Many drugs of abuse (DoA) are tested in urine samples. This testing is frequently hampered by analyte related molecules or drug metabolites that cross-react with the employed antibodies, causing false positive results. With a suitable pretreatment the interfering molecules can be removed and a reliable assay performed thereafter.

On the other hand, many DoA assay suffer from lack of sensitivity which may lead to false negative results. Here, the urine sample can be directed into a column where drug molecules are retained, and then eluted with a smaller volume than the original samples. Thus better sensitivity and higher reliability is achieved.

One aspect of the invention is to enrich, purify or fractionate one or more analytes to be measured from a sample by retaining methods like immobilization, sieving or filtering.

Immobilization may be done on surfaces or by antibodies so that desired substances or matrix components are retained. Filtering, for example by membranes, may be used to separate and retain molecules of desired size. Cell separation can be performed by flow-through microchannels. Pretreatment may be divided or arranged in two separate phases including pretreatments such as: reagent addition+incubation to form complex, reagent addition+incubation with proteolytic or other enzymes to be removed later, removal of lipids (lipemia) and removal of hemoglobin or other interfering substances. In one embodiment, the substance or substances that are to be measured are not chemically or physically reacted, modified or altered so, that the information content of a small sample used in discrete analysis is maintained as unchanged as possible.

Alternatively the invention is based on picking desired substances from the sample in order to enrich the sample itself or, preferably the analyte to be measured directly. Different substance may require different pretreatment means, but the apparatus may be designed so that the pretreatment means such as columns can be easily changed according to assaying needs. The columns or other means may be disposable or reusable, and changed automatically.

One example of two-phase pretreatment involves a first step of processing of a sample to release a target analyte from components within a sample that bind or sequester the analyte, thereby increasing accessibility to the target analyte, followed by a second step of separating the target analyte from matrix as described in herein. An embodiment of such a two-phase pretreatment process is hemolysis of a whole blood sample, for example by use of (i) capillary device, for example a plastic or glass capillary tube with an inner diameter of about 1 mm, at room temperature capable of applying a sheering force to physically rupture cellular components, (ii) sonication, (iii) detergents or other chemicals to disrupt cell membranes, or (iv) mild heat, followed by processing using an affinity column or other preparatory column capable of capturing the analyte or matrix component(s).

In instrument and operational point of view some typical ranges and structures can be contemplated. However, the invention is not limited to below presented features. regarding operating temperatures: 37 degrees would be typical, and the range can theoretically be as wide as presented above. In practice, it would be extremely difficult to have the temperature equal to sample or room temperature as the temperature inside analyzer always differs from outside. The hemolyzing capillary could preferably be thermostated and standardized to a certain temperature. The capillary itself would probably be a stainless steel, polymeric or glass capillary. The inner diameter can be 1 mm, but also as small as 0.1 mm or less. The shape of the capillary could be a very short capillary or tube-like device with one or more tiny orifices, one after the other, where the sample is pressed through.

Using a shear force caused by a capillary is advantageously performed at room temperature or a temperature that is lower than disintegration temperature of the cells in the sample. For example compared to a heat shock method this method avoids any danger of disintegrating or damaging substances that are supposed to remain intact in the sample that is further processed or analyzed. Thus, hemolysis by shear force provides benefits over other methods described herein.

Instead of conventional capillary, a capillary slot formed between two parallel planar surfaces or a stack of such surfaces could be used. This kind of a structure provides a straight capillary slot. If the slot or slots are formed between concentric tubes, circular slots are formed. Further, it can be contemplated that the cross section of the slot or slots needed are formed to have any desired shape, but a simple slot or capillary would be probably easiest and cheapest to produce. One possible alternative is to use straining plate or successive plates with small holes and pump the sample through such structure. Even a fibrous, ceramic or other type of filter giving desired flow resistance that causes the required shear force might be feasible and easy to manufacture and replace as necessary.

Mechanical blood damage (hemolysis) has been considered to be a disadvantage in various contexts. It is known that blood cells disintegrate under mechanical stress. An experimental study between cell disintegration under laminar and turbulent flow has been conducted and the results are reported on *ASAIO Journal* 2004, *Effects of Turbulent Stresses upon Mechanical Hemolysis: Experimental and Computational Analysis.*

The idea of the invention is to use mechanical hemolysis in advantage as a pretreatment of blood samples.

The hemolysis effect of the capillary on treated blood cells in the sample depends on several factors. Some of these are the velocity of the flow, degree of turbulence, length of the capillary, diameter of the capillary and the material of the capillary. Since these variable each effect of others mentioned, definite values of dimensioning the capillary is difficult to give and dimensions given herein are only explanatory.

In a discrete analysis several measurements may be done from a single sample. To accomplish this using the present invention, a sub-sample is removed from the primary sample and the pretreatment is done on the subsample, leaving the primary sample unchanged. Thus, the primary sample may be used for further analyses of other substances.

One aspect of the invention is to combine above described pretreatment methods with a discrete analysis apparatus. The idea is that pretreatment step operates integrated with the analyzer so that pretreatment can be performed only when the analyzer receives such a test request that includes a pretreatment step. The pretreatment step operates independently from the analyzer so that normal analyzing processes can be done simultaneously with the pretreatment. The analyzer performs requested measurements for each sample or subsample (sample aliquot) regardless whether the sample/subsample has been pretreated or not. Also, some of the subsamples of one sample analyte may be pretreated and some not, exactly as required. As the pretreatment step does not interfere with the measurements performed by the analyzer, several measurement cycles may occur simultaneously in the analyzer.

According to one valuable aspect of the invention, the invention utilizes a discrete fluid analyzing apparatus, wherein measurements are done photoelecmetrically or electrochemically on samples placed in separate wells. Reactants are used as needed to induce changes in the analyte in order to obtain response that can be measured photoelecmetrically or electrochemically. This type of measurement system is relatively inexpensive. Therefore inexpensive ways to handle the analyte samples and subsamples are preferably used. For example, washable dispensers are used instead of disposable ones. This limits the invention to measurements wherein contamination, cross-contamination or mixing of samples can be avoided to a level that does not interfere with the measurements by washing and cleaning the dispensers or other fluid transfer means, such as dispensing needles, probes or washable pipette tips.

The sample or a subsample taken from it undergoes changes during measurement step when reactants are used. Therefore the molecule (analyte) to be measured must not change chemically under the pretreatment step. This is a requirement for the pretreatment step to operate properly with a discrete analyzer.

Figure 3:
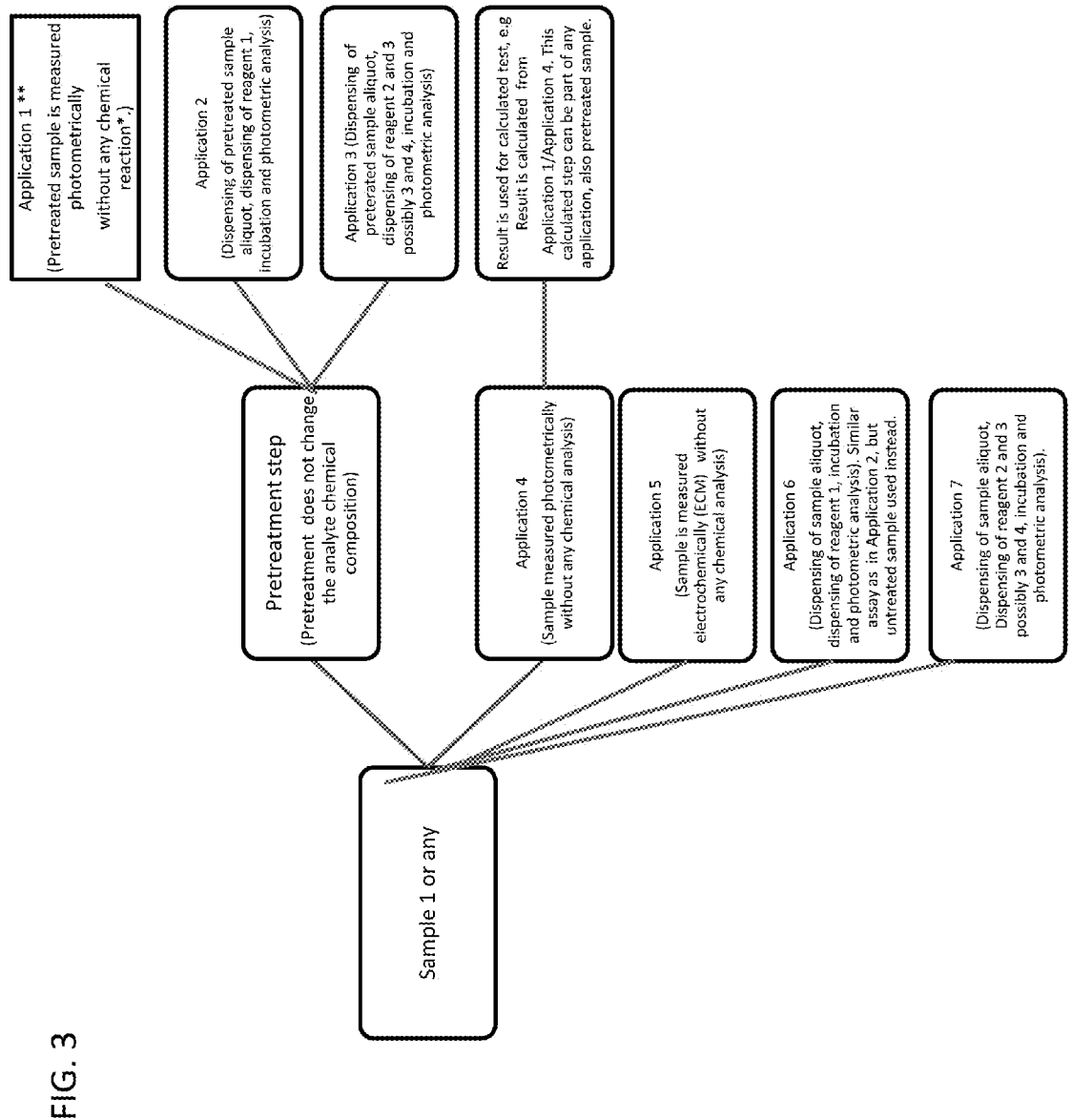
FIG. 3 shows a flow diagram of one operation workflow of the invention.

FIG. 3 shows an example of some workflows that can be accomplished by the invention. First, a sample 1 is obtained. The sample may be any liquid sample, for example beer, wort, blood or urine. The sample is identified by a data carrier such as a RFID chip or bar code and when the sample vessel enters the analyzer, data is read, or the sample can be identified to the system manually by the user, the sample is identified and the operating system of the analyzer requests all pretreatments and measurements that are to be performed on the sample. The sample may be placed on queue or taken directly forwards. Now the whole sample or more commonly one or more subsamples are taken from the sample by a metallic needle and the extracted liquid is placed on measurement wells, such as cuvettes.

If pretreatment is needed, the sample or subsample/aliquot is transferred to pretreatment step and pretreatment is performed as earlier has been described. In short, pretreatment includes capturing and releasing molecule that is to be measured in order to purify or enrich it. See description of pretreatment process for further details. Pretreatment should not change the chemical composition of the analyte. The pretreated sample is transferred to a measurement step. Some examples are shown in FIG. 3. In Application 1, the sample (herein a whole sample, alternatively a subsample) can be measured photometrically without any chemical reaction. In this example, pretreatment is part of the Application and is automatically generated by requesting the Application 1.

In practice this application consists of pretreatment step with flexibility to design pretreatment parameters and the actual measurement step. In this case measurement is performed with no reagent additions. Application 1 can be for example beer/wort bitterness or polyphenol analysis.

Applications 2 and 3 include dispensing at least sample aliquot (subsample), dispensing reagent, incubation and photometric analysis. In Application 3, two or more reagents are used (reagents 2, 3, 4, and 5).

When pretreatment step is not needed, sample or sample aliquot can be processed according to Applications 4-7. Now the sample/subsample (aliquot) is measured photometrically without reacting with a reagent (Application 4), measured electrochemically without adding reagent (Application 5) or by similar methods as in Applications 2 and 3 (Applications 6 and 7). The Applications shown here are examples only and any measurement process application available in analyzer may be used in conjunction with both pretreatment steps, i.e. together with actual pretreatment or directing the sample or subsample directly to measurement step.

Applications 2-7 can be, for example, Beta-Glucan, Glucose, pH, conductivity, hemoglobin, HbA1C analysis, Ammonia or sulfate measurements.

Several samples, and their replicates, can be assayed simultaneously with several applications.

Sample dispensing does not require disposable tips. Vice versa, disposable tips should be avoided in order to keep the operating costs at bay. Application examples can have flexibility for volumes, dispensing orders and include e.g. additional sample blankings.

Figure 4:
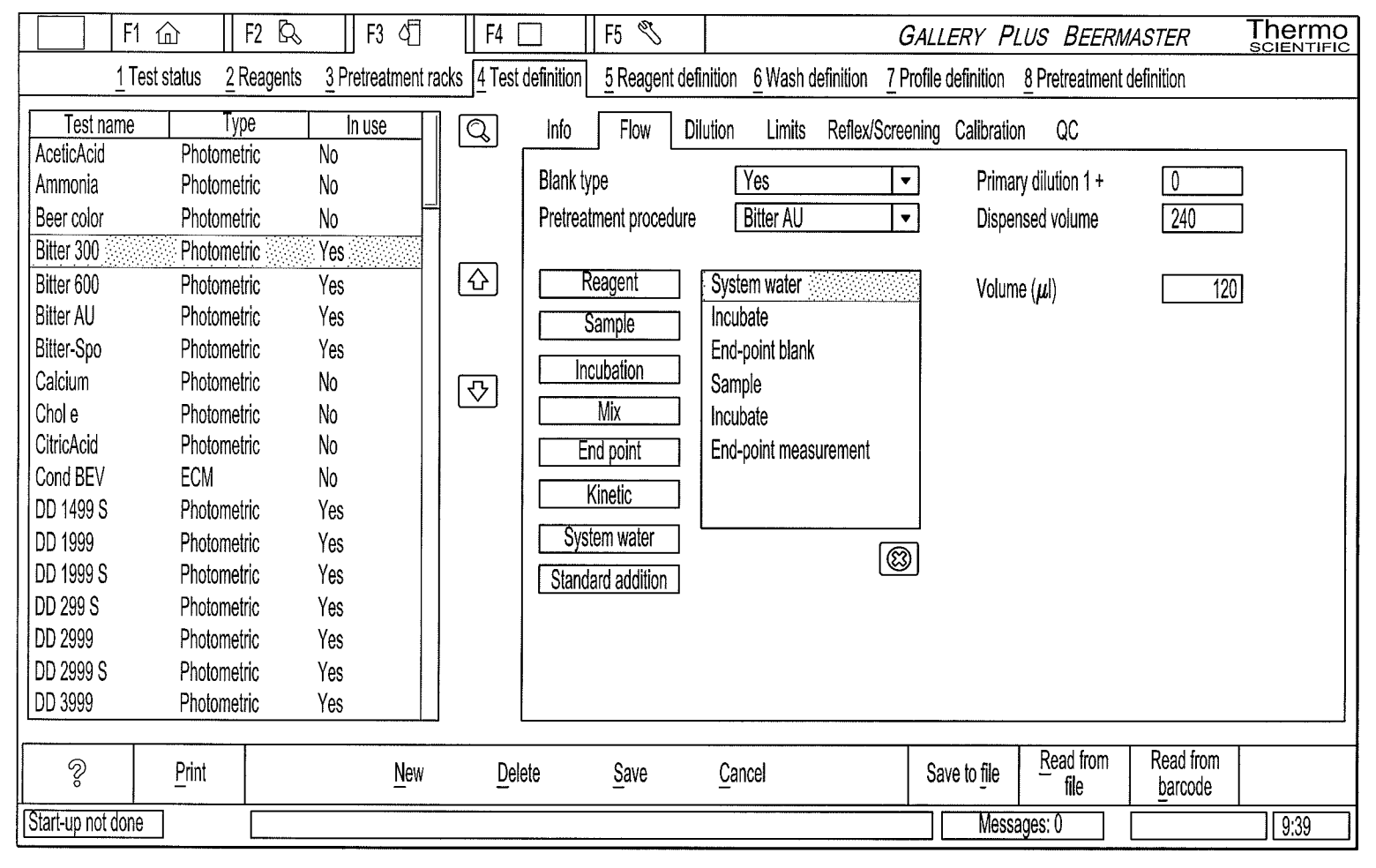

FIG. 4 shows one operating principle of the invention using an explanatory display template. Herein the process starts when client requests a test. This request can be delivered to the analyzer by a memory device or made manually when a sample is loaded to the analyzer. When a test is requested for a named sample, the analyzer automatically selects a pretreatment step including pretreatment or no pretreatment according to the specifications of the test as well as measurements, reagents, incubation time, mixing and other features. All parameters may be determined flexibly.

The left side of the display shows a list of test and treatments available. Herein a test Bitter 300 is requested (highlighted). The list shows that the test is photometric and pretreatment is on use. On the right side is information about the test which shows that pretreatment method is Bitter AU. Further details about reagents, samples, incubation and such used in a particular test are placed under tabs with same nominations (now shown in this display). The flow of the test is displayed on the right side of the tabs.

As can be seen on the display, Bitter 300 request performs automatically a Bitter AU pretreatment (selection: Pretreatment procedure: Bitter AU) and thereafter a photometric test typical to a discrete analyzer. The parameters of the photometric test are placed under the tabs bearing nominations of the parameters.

Multiple tests may be performed on one sample. As can be seen on the left side of the display, the analyzer is capable of performing multiple different tests (see test name) simultaneously and some of the tests may include pretreatment and some not. A pretreatment step can also be performed without a following photometric test requiring additional reagents. Usually, a subsample of the original or pretreated sample is needed for each test.

Various embodiments of the method according to the invention are capable of performing optional, on demand pretreatment, simultaneous measurement and pretreatment, and/or measurement. Pretreatment may be performed on a whole sample or subsample or sample aliquot of the whole sample. Several tests may be performed on a single sample. Sample or sample aliquot can also be automatically treated or e.g. adjusted for pH by reagent addition before pretreatment.

Numerous embodiments of the present invention have been shown and described with attention paid to fundamental novel features of the invention as applied to the embodiments. However, it is understood that various omissions and substitutions and changes in the form and details of the invention may be made by those skilled in the art without departing from the spirit of the invention. For example, it is expressly intended that all combinations of those elements which perform substantially the same results are within the scope of the invention. Substitutions of the elements from one described embodiment to another are also fully intended and contemplated. It is also to be understood that the drawings are not necessarily drawn to scale but they are merely conceptual in nature. It is the intention, therefore, to be limited only as indicated by the scope of the claims appended hereto.

What is claimed is:

1. Method for pretreatment of a sample of whole blood in an automated discrete fluid analyzing apparatus, comprising:
the automated discrete fluid analyzing apparatus performing at least each of the following steps in an automated fashion:
producing a hemolyzed subsample and a non-hemolyzed sample portion by hemolyzing at least a subsample of the sample, and
pretreating the hemolyzed subsample by retaining at least one substance or an analyte from the hemolyzed subsample by using capture means within the automated discrete fluid analyzing apparatus, whereby the at least one substance or analyte is reversibly removable, and
eluting the at least one substance or the analyte from the capture means within the automated discrete fluid apparatus.

2. The method according to the claim 1, wherein the step of hemolyzing at least the subsample of the sample is performed by using a capillary device at a temperature below disintegration temperature of blood cells in the sample prior to immobilizing the at least one substance or the analyte.

3. The method according to claim 1, wherein the step of hemolyzing at least the subsample is performed by applying shear forces sufficient to rupture cellular components.

4. The method according to claim 3, wherein the shear forces are applied to the subsample by use of a capillary device at a temperature below disintegration temperature of the cellular components in the subsample.

5. The method according to claim 1, the method further comprising the steps of:
analyzing the at least one substance or the analyte,
wherein the steps of eluting and analyzing are performed as a function of the automated discrete fluid analyzing apparatus.

6. The method according to the claim 1, wherein the at least one substance is an analysis interfering substance, the method further comprising:
eluting and discarding the analysis interfering substance using the automated discrete fluid analyzing apparatus.

7. The method according to the claim 1, the method further comprising the step of: regenerating the capture means.

8. The method according to claim 1, wherein the capture means does not chemically alter the at least one substance or the analyte.

9. The method according to claim 1, the method further comprising:
immobilizing the at least one substance or the analyte by binding the at least one substance or the analyte to an antibody or other specifically binding substance.

10. The method according to claim 1, wherein the hemolyzed subsample comprises a first volume, and only the analyte from the hemolyzed subsample is retained by the capture means; the method further comprising the step of:
eluting the analyte in a second volume that is smaller than the first volume.

11. The method according to claim 1, the method further comprising at least one of the following steps using the automated discrete fluid analyzing apparatus:
   separating the analyte from cell debris in the sub-sample,
   separating the analyte from an analyte interfering substance,
   desalting the sample,
   exchanging a solvent of the sample, and
   separating the analyte from a matrix substance.

12. The method according to claim 1, the method further comprising: immobilizing at least the one substance or the analyte by using at least one of the following methods or properties:
   performing reversible covalent bonding,
   performing ionic interaction,
   sieving or filtering the at least one substance or the analtye by size or shape of molecules thereof or by diffusion, and
   using polarity, hydrophobicity, molecule interaction or group specific interaction and chiral recognition.

13. The method according to claim 1, the method further comprising:
   using the automated discrete fluid analyzing apparatus to perform at least one of a chemical reactions and a photometric measurement on at least one of the non-pretreated subsamples or the non-pretreated samples in one or more separate wells of the automated discrete fluid analyzing apparatus.

14. The method according to claim 1, the method further comprising:
   dispensing at least one reagent to the hemolyzed subsample, and
   photometrically measuring at least one property of the hemolyzed subsample using the automated discrete fluid analyzing apparatus.

15. The method according to claim 1, the method further comprising:
   after performing the measuring step, transferring and dispensing the sample and the subsample using at least one washable pipette tips dispenser.

16. The method according to claim 1, the method further comprising:
   performing at least two different measurements on the sample simultaneously or consecutively.

17. The method according to claim 1, the method further comprising:
   using an automated discrete photometric analyzing device for measuring and pretreating the sample, and
   immobilizing the at least one substance or the analyte from the subsample.

18. The method of claim 1, further comprising: measuring at least one property of the hemolyzed subsample in a first measuring step, and simultaneously with or consecutively to the first measuring step, directing the non-hemolyzed sample portion to a second measuring step to measure at least one property of the non-hemolyzed sample portion.

19. The method according to claim 18, wherein at least one of the first measuring step and the second measuring step is performed chemically or photometrically.

20. The method according to claim 18, wherein the first measuring step and the second measuring step are performed using the automated discrete fluid analyzing apparatus.

21. The method according to claim 18, where the first measuring step is performed directly after the pretreating step.

22. Method for pretreatment of a sample of whole blood in an automated discrete fluid analyzing apparatus, comprising:
   the automated discrete fluid analyzing apparatus performing at least each of the following steps in an automated fashion:
   hemolyzing at least a subsample of the sample, and
   pretreating the hemolyzed subsample by retaining at least one substance or an analyte from the hemolyzed subsample by using capture means within the automated discrete fluid analyzing apparatus, whereby the at least one substance or analyte is reversibly removable,
   eluting the at least one substance or the analyte from the capture means within the automated discrete fluid apparatus,
   measuring at least one property of the subsample, and
   simultaneously or consecutively directing non-pretreated samples or non-pretreated subsamples to the measuring step.

23. The method according to claim 22, the method further comprising:
   using the automated discrete fluid analyzing apparatus to perform at least one of a chemical reactions and a photometric measurement on at least one of the non-pretreated subsamples or the non-pretreated samples in one or more separate wells of the automated discrete fluid analyzing apparatus.

24. The method of claim 22 wherein the step of hemolyzing at least a subsample of the sample produces a hemolyzed subsample and a non-hemolyzed sample portion.

25. The method according to the claim 22, wherein the step of hemolyzing at least the subsample of the sample is performed by using a capillary device at a temperature below disintegration temperature of blood cells in the sample prior to immobilizing the at least one substance or the analyte.

26. The method according to claim 22, wherein the hemolyzed subsample comprises a first volume, and only the analyte from the hemolyzed subsample is retained by the capture means; the method further comprising the step of:
   eluting the analyte in a second volume that is smaller than the first volume.

27. The method according to the claim 22, wherein the at least one substance is an analysis interfering substance, the method further comprising:
   eluting and discarding the analysis interfering substance using the automated discrete fluid analyzing apparatus.

28. Method for pretreatment of a sample of whole blood in an automated discrete fluid analyzing apparatus, comprising:
   the automated discrete fluid analyzing apparatus performing at least each of the following steps in an automated fashion:
   hemolyzing at least a subsample of the sample, and
   pretreating the hemolyzed subsample by retaining at least one substance or an analyte from the hemolyzed subsample by using capture means within the automated discrete fluid analyzing apparatus, whereby the at least one substance or analyte is reversibly removable, and
   eluting the at least one substance or the analyte from the capture means within the automated discrete fluid apparatus,
   wherein the step of hemolyzing at least the subsample of the sample is performed by using a capillary device at a temperature below disintegration temperature of blood cells in the sample prior to immobilizing the at least one substance or the analyte.

29. The method of claim 28 wherein the step of hemolyzing at least a subsample of the sample produces a hemolyzed subsample and a non-hemolyzed sample portion.

30. The method according to claim 28, the method further comprising at least the steps of:
   measuring at least one property of the subsample, and
   simultaneously or consecutively directing non-pretreated samples or non-pretreated subsamples to the measuring step.

31. The method according to claim 28, wherein the hemolyzed subsample comprises a first volume, and only the analyte from the hemolyzed subsample is retained by the capture means; the method further comprising the step of:
   eluting the analyte in a second volume that is smaller than the first volume.

32. The method according to the claim 28, wherein the at least one substance is an analysis interfering substance, the method further comprising:
   eluting and discarding the analysis interfering substance using the automated discrete fluid analyzing apparatus.

33. The method according to claim 28, the method further comprising the steps of:
   analyzing the at least one substance or the analyte,
   wherein the steps of eluting and analyzing are performed as a function of the automated discrete fluid analyzing apparatus.

34. Method for pretreatment of a sample of whole blood in an automated discrete fluid analyzing apparatus, comprising:
   the automated discrete fluid analyzing apparatus performing at least each of the following steps in an automated fashion:
   hemolyzing at least a subsample of the sample, and
   pretreating the hemolyzed subsample by retaining at least one substance or an analyte from the hemolyzed subsample by using capture means within the automated discrete fluid analyzing apparatus, whereby the at least one substance or analyte is reversibly removable, and
   eluting the at least one substance or the analyte from the capture means within the automated discrete fluid apparatus
   wherein the hemolyzed subsample comprises a first volume, and only the analyte from the hemolyzed subsample is retained by the capture means; the method further comprising the step of:
   eluting the analyte in a second volume that is smaller than the first volume.

35. The method according to the claim 34, wherein the step of hemolyzing at least the subsample of the sample is performed by using a capillary device at a temperature below disintegration temperature of blood cells in the sample prior to immobilizing the at least one substance or the analyte.

36. The method according to the claim 34, wherein the at least one substance is an analysis interfering substance, the method further comprising:
   eluting and discarding the analysis interfering substance using the automated discrete fluid analyzing apparatus.

37. The method according to claim 34, the method further comprising at least the steps of:
   measuring at least one property of the subsample, and
   simultaneously or consecutively directing non-pretreated samples or non-pretreated subsamples to the measuring step.

38. The method according to claim 34, the method further comprising:
   using the automated discrete fluid analyzing apparatus to perform at least one of a chemical reactions and a photometric measurement on at least one of the non-pretreated subsamples or the non-pretreated samples in one or more separate wells of the automated discrete fluid analyzing apparatus.

* * * * *